United States Patent [19]
Nakatani et al.

[11] Patent Number: 5,886,152
[45] Date of Patent: Mar. 23, 1999

[54] HUMANIZED B-B10

[75] Inventors: Tomoyuki Nakatani, Kawanishi; Hideyuki Gomi, Nagaokakyou, both of Japan; John Wijdenes, Larnod, France; Hiroshi Noguchi, Kawanishi, Japan

[73] Assignees: Sumitomo Pharmaceuticals Company, Limited, Osaka, Japan; Biotest Pharma GbmH, Germany; Diaclone, Cedex, France

[21] Appl. No.: 232,081

[22] PCT Filed: Dec. 3, 1992

[86] PCT No.: PCT/JP92/01583

§ 371 Date: May 10, 1994

§ 102(e) Date: May 10, 1994

[87] PCT Pub. No.: WO93/11238

PCT Pub. Date: Jun. 10, 1993

[30] Foreign Application Priority Data

Dec. 6, 1991 [JP] Japan ................................. 3-323319

[51] Int. Cl.$^6$ ..................... C07K 16/46; A61K 39/395; C07H 21/04
[52] U.S. Cl. ..................... 530/387.3; 530/387.1; 530/388.1; 530/388.22; 435/69.7; 435/328; 536/23.53; 424/130.1; 424/133.1; 424/135.1; 424/134.1
[58] Field of Search ............... 424/130.1, 133.1, 424/135.1, 134.1, 143.1; 536/23.53; 530/387.1, 387.3, 388.1, 388.22; 435/69.1, 69.7, 70.21, 240.27, 328

[56] References Cited

U.S. PATENT DOCUMENTS 5,084,391  1/1992  Wijdenes et al. .
5,132,405  7/1992  Huston et al. ................ 530/387.3
5,530,101  6/1996  Queen et al. ................. 530/387.3

FOREIGN PATENT DOCUMENTS 0239400  5/1990  European Pat. Off. .
0328404  10/1992  European Pat. Off. .

OTHER PUBLICATIONS

Harris et al. [(TIBECH 11:42–44 (1993)].
Tiberghien et al. Transplantation 52:475–480 (1991).
Wijdenes et al. [Blood 75:1017–1023 (1990)].
Queen et al. [PNAS 86:10029–10033 (1989)].
Jones et al., Nature, 321, 522–525 (1986).
Riechmann et al., Nature, 332, 323–327 (1988).
Man Sung Co et al., Proc. Natl. Acad. Sci. USA, 88, 2869–2873, (1991).
Tempest et al., Biotechnology, 9, 266–271 (1991).
Gorman et al., Proc. Natl. Acad. Sci. USA, 88, 4181–4185 (1991).
Chothia et al., J. Mol. Biol. 196, 901–917 (1987).
Chothia et al., Nature, 342, 877–883 (1989).
Tramontano et al., J. Mol. Biol., 215, 175–182 (1990).
Hale et al., The Lancet, 2, 1394–1399 (1988).
Verhoeyen et al., Science, 239, 1534–1536 (1988).
The Lancet, 337, 1411–1412 (1991).
Kettleborough et al., Protein Engineering, 4, No. 7, 773–783 (1991).
Hakimi et al., J. Immunology, 147, 1352–1359 (1991).
Junghans et al., Cancer Research, 50, 1495–1502 (1990).
Brown et al., Proc. Natl. Acad. Sci. USA, 88, 2663–2667 (1991).
Maeda et al., Hum. Antibod. Hybridomas, 2, 124–134 (1991).
Daugherty et al., Nucleic Acids Research, 19, 2471–2476 (1991).
Lewis et al., Gene, 101, 297–302 (1991).

*Primary Examiner*—Frank C. Eisenschenk
*Attorney, Agent, or Firm*—Birch Stewart Kolasch & Birch, LLP

[57] ABSTRACT

A humanized antibody is provided, which is obtained by transplantation of the complementarity determining region of a mouse monoclonal antibody B-B10 specific to a human IL-2 receptor into a human antibody. The antibody has a very low antigenicity, and therefore, it is useful for treatment of carcinoma expressing IL-2 receptor.

12 Claims, 9 Drawing Sheets

Figure 1

```
        10         20         30         40
GAGGTGCAGCTGCAGCAGTCAGGGGCAGAGCTTGTGAAGTCAGGGGCC
GluValGlnLeuGlnGlnSerGlyAlaGluLeuValLysSerGlyAla 50         60         70         80         90
TCAGTCAAGTTGTCCTGTACAGCTTCTGGCTTCAACATTAAAGACACC
SerValLysLeuSerCysThrAlaSerGlyPheAsnIleLysAspThr 100        110        120        130        140
TATATGCACTGGGTGAAGCAGAGGCCTGAACAGGGCCTGGAGTGGATT
TyrMetHisTrpValLysGlnArgProGluGlnGlyLeuGluTrpIle 150        160        170        180        190
GGAAGAATTAATCCTACGAATGGTAATACTAAATATGACCCGAAGTTC
GlyArgIleAsnProThrAsnGlyAsnThrLysTyrAspProLysPhe 200        210        220        230        240
CAGGGCAAGGCCACTGTGACAGCAGACACATCCTCCAACACAGCCTAC
GlnGlyLysAlaThrValThrAlaAspThrSerSerAsnThrAlaTyr 250        260        270        280
CTGCAGCTCGGCAGCCTGACATCTGAGGACACTGCCGTCTATTACTGT
LeuGlnLeuGlySerLeuThrSerGluAspThrAlaValTyrTyrCys 290        300        310        320        330
GCTAGGAGGGGGGATGCCATGTACTTCGATGTCTGGGGCGCAGGGACC
AlaArgArgGlyAspAlaMetTyrPheAspValTrpGlyAlaGlyThr 340        350
ACGGTCACCGTCTCCTCA
ThrValThrValSerSer
```

Figure 2

```
        10        20        30        40
GACATCTTGCTGACTCAGTCTCCAGCCATCCTGTCTGTGAGTCCAGGA
AspIleLeuLeuThrGlnSerProAlaIleLeuSerValSerProGly 50        60        70        80        90
GAAAGAGTCAGTTTCTCCTGCAGGGCCAGTCAGACCATTGGCACAAGC
GluArgValSerPheSerCysArgAlaSerGlnThrIleGlyThrSer 100       110       120       130       140
ATACACTGGTATCAGCGAAGAACAAATGGTTCTCCAAGGCTTCTCATA
IleHisTrpTyrGlnArgArgThrAsnGlySerProArgLeuLeuIle 150       160       170       180       190
AAGTATGCTTCTGAGTCTATCTCTGGGATCCCTTCCAGGTTTAGTGGC
LysTyrAlaSerGluSerIleSerGlyIleProSerArgPheSerGly 200       210       220       230       240
AGTGGATCAGGGACAGATTTTACTCTTAGCATCAACAGTGTGGAGTCT
SerGlySerGlyThrAspPheThrLeuSerIleAsnSerValGluSer 250       260       270       280
GAAGATATTGCAGATTATTACTGTCAACAAAGTAGTAGCTGGCCGCTC
GluAspIleAlaAspTyrTyrCysGlnGlnSerSerSerTrpProLeu 290       300       310       320
ACGTTCGGTGCTGGGACCAAGCTGGAGCTGAAA
ThrPheGlyAlaGlyThrLysLeuGluLeuLys
```

Figure 3

```
<VH>
            FR1                              CDR1    FR2
mB-B10   EVQLQQSGAELVKSGASVKLSCTASGFNIK      DTYMH   WVKQRPEQGL
hB-B10   EVHLVQSGAEVKKPGSSVKVSCKASGFNIK      DTYMH   WVRQAPGQGL
KAS      EVHLVQSGAEVKKPGSSVKVSCKASGGTFS      SYAIS   WVRQAPGQGL

CDR2                    FR3
              M1                      M2
mB-B10   EWIG  RINPTNGNTKYDPKFQG       KATVTADTSSNTAYLQLGSLTSED
hB-B10   EWMG  RINPTNGNTKYDPKFQG       RVTITADESTNTAYMELRSLRSDD
KAS      EWMG  GIIPIFGQANYAQKFQG       RVTITADESTNTAYMELRSLRSDD

CDR3            FR4
                                  M3
mB-B10   TAVYYCAR  RGDAMY---FDV   WGAGTTVTVSS
hB-B10   TAMYYCAR  RGDAMY---FDV   WGQGTLVTVSS
KAS      TAMYYCAK  EGYGDYGRPFDF   WGQGTLVTVSS

<VK>
            FR1                       CDR1           FR2
         M4
mB-B10   DILLTQSPAILSVSPGERVSFSC      RASQTIGTS-IH   WYQRRTNGSP
hB-B10   EIVLTQSPGTLSLSPGERATLSC      RASQTIGTS-IH   WYQQRPGQAP
PAY      EIVLTQSPGTLSLSPGERATLSC      RASQSVSSSYLA   WYQQRPGQAP

CDR2       FR3
           M5
mB-B10   RLLIK   YASESIS   GIPSRFSGSGSGTDFTLSINSVESEDIADYYC
hB-B10   RLLIY   YASESIS   GIPDRFSGSGSGTDFTLTISRLEPEDFAVYYC
PAY      RLLIY   GASSRAT   GIPDRFSGSGSGTDFTLTISRLEPEDFAVYYC

CDR3         FR4
mB-B10   QQSSSWPLT    FGAGTKLELK
hB-B10   QQSSSWPLT    FGQGTKVEIK
PAY      QQYGSSPLT    FGQGTKVEIK
```

Figure 4

```
              10         20         30         40         50
5' GAGGAGCTCC AGACAATGTC TGTCTCCTTC CTCATCTTCC TGCCCGTGCT
3' CTCCTCGAGG TCTGTTACAG ACAGAGGAAG GAGTAGAAGG ACGGGCACGA 60         70         80         90        100
   GGGCCTCCCA TGGGGTCAGT GTCAGGGAGA TGCCGTATTC ACAGCAGCAT
   CCCGGAGGGT ACCCCAGTCA CAGTCCCTCT ACGGCATAAG TGTCGTCGTA 110        120        130        140        150
   TCACAGACTG AGGGGTGTTT CACTTTGCTG TTTCCTTTTG TCTCCAGGTG
   AGTGTCTGAC TCCCCACAAA GTGAAACGAC AAAGGAAAAC AGAGGTCCAC 160        170        180        190        200
   TCCTGTCAGA GGTGCACCTG GTCCAGTCAG GGCAGAGGT CAAGAAGCCA
   AGGACAGTCT CCACGTGGAC CAGGTCAGTC CCCGTCTCCA GTTCTTCGGT 210        220        230        240        250
   GGGTCCTCAG TCAAGGTCTC CTGTAAGGCT TCTGGCTTCA ACATTAAAGA
   CCCAGGAGTC AGTTCCAGAG GACATTCCGA AGACCGAAGT TGTAATTTCT 260        270        280        290        300
   CACCTATATG CACTGGGTGA GGCAGGCCCC TGGGCAGGGC CTGGAGTGGA
   GTGGATATAC GTGACCCACT CCGTCCGGGG ACCCGTCCCG GACCTCACCT 310        320        330        340        350
   TGGGAAGAAT TAATCCTACG AATGGTAATA CTAAATATGA CCCGAAGTTC
   ACCCTTCTTA ATTAGGATGC TTACCATTAT GATTTATACT GGGCTTCAAG 360        370        380        390        400
   CAGGGCAGGG TCACTATTAC AGCAGACGAG TCCACAAACA CAGCCTACAT
   GTCCCGTCCC AGTGATAATG TCGTCTGCTC AGGTGTTTGT GTCGGATGTA 410        420        430        440        450
   GGAGCTGAGG AGCCTGAGGT CTGATGACAC TGCCATGTAT TACTGTGCTA
   CCTCGACTCC TCGGACTCCA GACTACTGTG ACGGTACATA ATGACACGAT 460        470        480        490        500
   GGAGGGGGGA TGCCATGTAC TTCGATGTCT GGGGCCAAGG CACCCTGGTC
   CCTCCCCCCT ACGGTACATG AAGCTACAGA CCCCGGTTCC GTGGGACCAG 510        520        530
   ACCGTCTCCT CAGGTAAGAA TGGCCAAGCT TG   3'
   TGGCAGAGGA GTCCATTCTT ACCGGTTCGA AC   5'
```

Figure 5

```
            10         20         30         40         50
5' GGAGGATCCA ATTATCTGCT GACTTATAAT ACTACTAGAA AGCAAATTTA
3' CCTCCTAGGT TAATAGACGA CTGAATATTA TGATGATCTT TCGTTTAAAT 60         70         80         90        100
   AATGACATAT TTCAATTATA TCTGAGACAG CGTGTATAAG TTTATGTATA
   TTACTGTATA AAGTTAATAT AGACTCTGTC GCACATATTC AAATACATAT 110        120        130        140        150
   ATCATTGTCC ATTCCTGACT ACAGGTGCCT ACGGGAGAT CGTCCTGACT
   TAGTAACAGG TAAGGACTGA TGTCCACGGA TGCCCCTCTA GCAGGACTGA 160        170        180        190        200
   CAGTCTCCAG GCACACTGTC TCTGAGTCCA GGAGAAAGAG CCACACTGTC
   GTCAGAGGTC CGTGTGACAG AGACTCAGGT CCTCTTTCTC GGTGTGACAG 210        220        230        240        250
   CTGCAGGGCC AGTCAGACCA TTGGCACAAG CATACACTGG TATCAGCAGA
   GACGTCCCGG TCAGTCTGGT AACCGTGTTC GTATGTGACC ATAGTCGTCT 260        270        280        290        300
   GACCAGGCCA GGCCCCAAGG CTTCTCATAT ATTATGCTTC TGAGTCTATC
   CTGGTCCGGT CCGGGGTTCC GAAGAGTATA TAATACGAAG ACTCAGATAG 310        320        330        340        350
   TCTGGCATCC CTGATAGGTT TAGTGGCAGT GGATCAGGGA CAGATTTTAC
   AGACCGTAGG GACTATCCAA ATCACCGTCA CCTAGTCCCT GTCTAAAATG 360        370        380        390        400
   TCTTACAATC TCCAGGCTGG AGCCAGAAGA TTTCGCAGTC TATTACTGTC
   AGAATGTTAG AGGTCCGACC TCGGTCTTCT AAAGCGTCAG ATAATGACAG 410        420        430        440        450
   AACAAAGTAG TAGCTGGCCG CTCACGTTCG GTCAGGGGAC CAAGGTCGAG
   TTGTTTCATC ATCGACCGGC GAGTGCAAGC CAGTCCCCTG GTTCCAGCTC 460        470        480
   ATAAACGTG AGTAGAATTT AAATTTTAAG CTTCTT     3'
   TATTTGCAC TCATCTTAAA TTTAAAATTC GAAGAA     5'
```

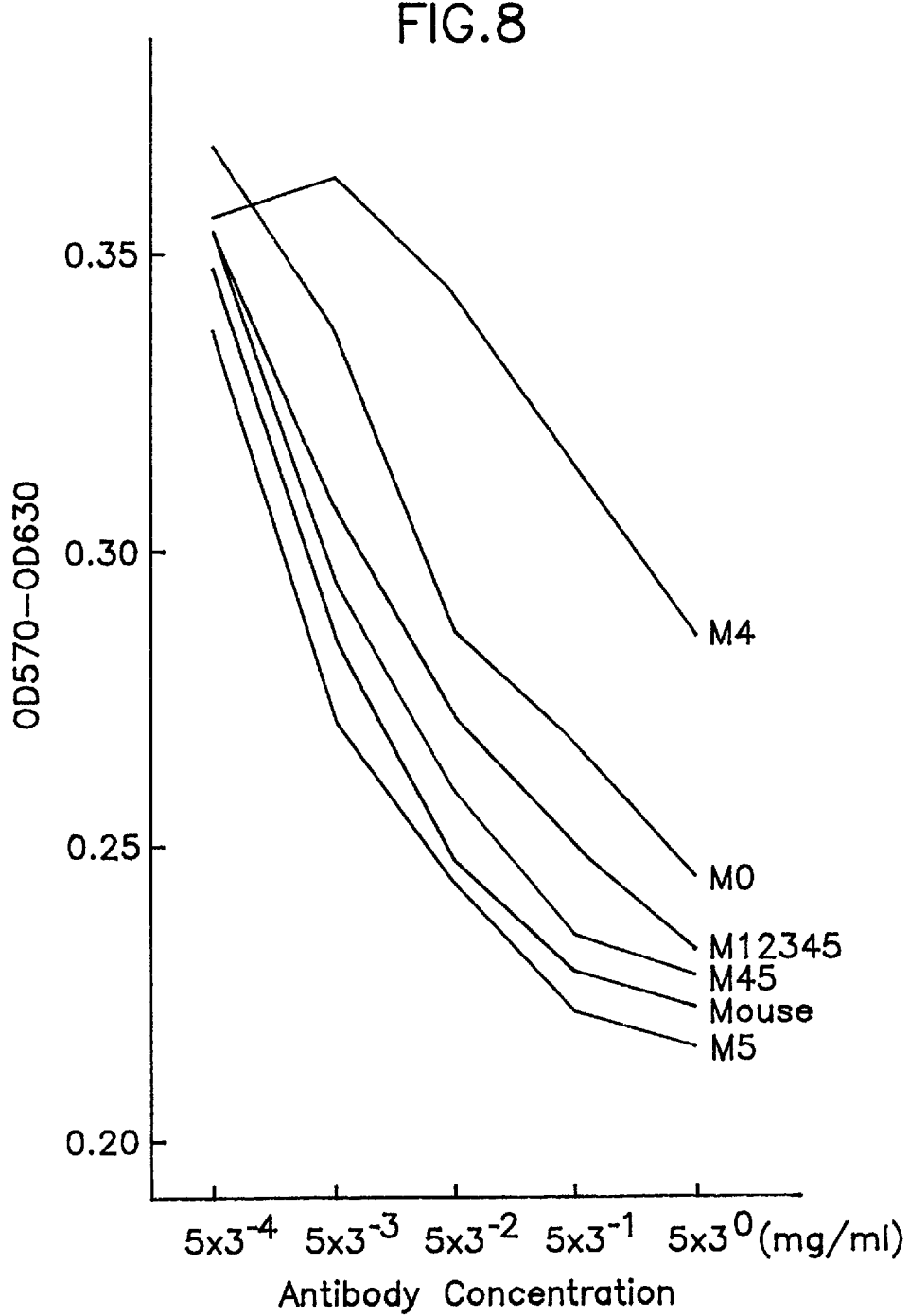

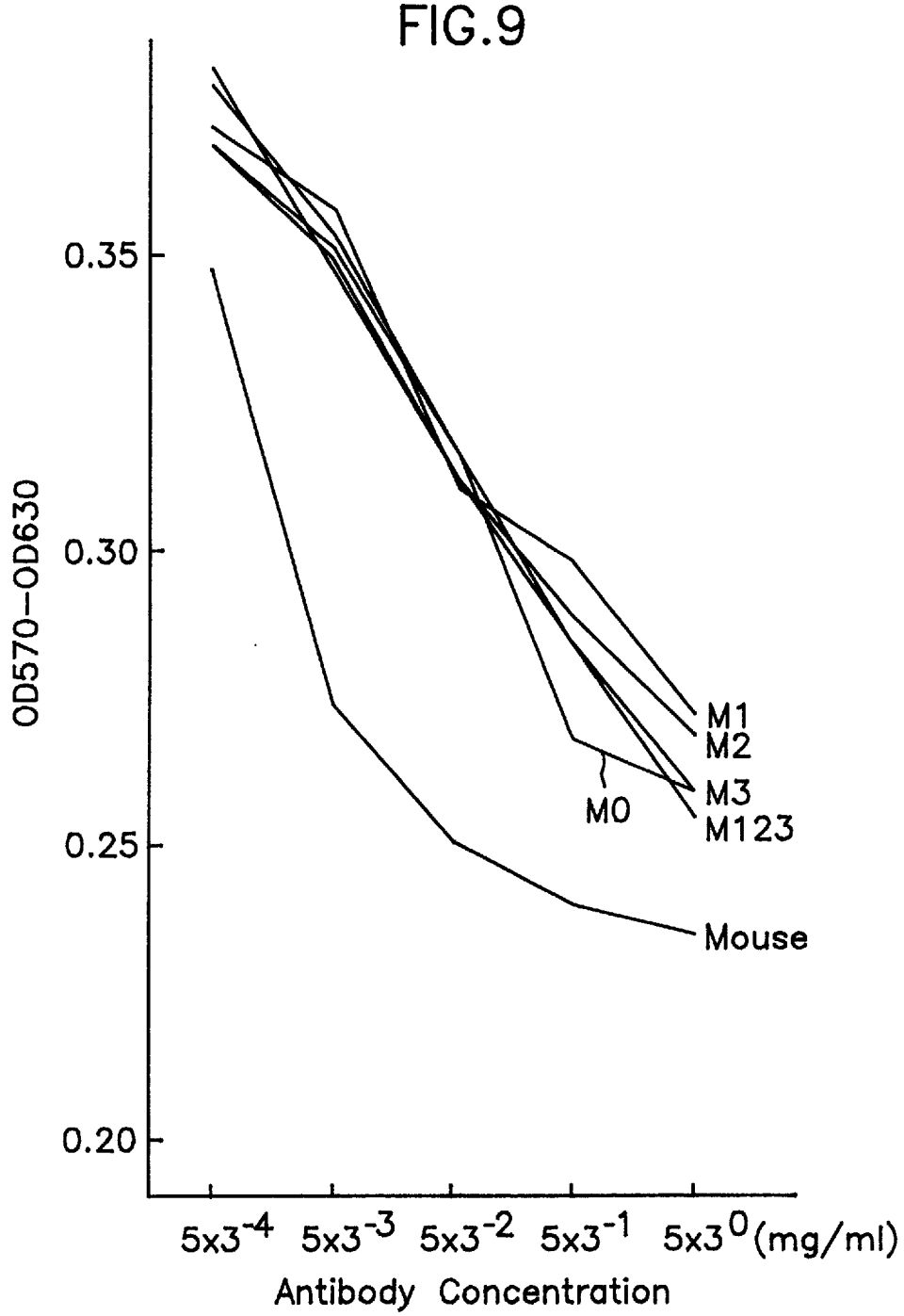

ized B-B10

HUMANIZED B-B10

FIELD OF THE INVENTION

The present invention relates to a humanized antibody specific to a human IL-2 receptor. More particularly, it relates to a humanized antibody obtained by transplantation of the complementarity- determining region (hereinafter, referred to as CDR) of a mouse monoclonal antibody B-B10 specific to a human IL-2 receptor into a human antibody, and a composition comprising said antibody as an active ingredient.

BACKGROUND OF THE INVENTION

The structure and function of the antibody related to the present invention will be first explained. Namely, such structure and function are described in details in Kabat et al.: Sequences of proteins of immunological interest, 4th Ed., 1989, NIH, U.S.A. as well as Roitt et al.: Immunology, 2nd Ed., 1989, Gower Medical Publishing, U.S.A. & U.K.

The antibody (immunoglobulin) is an antigen-specific glycoprotein as produced by B lymphocytes when a subject is sensitized with an antigen which is a foreign substance to the subject. As the human immunoglobulin, there are known 5 classes, i.e., IgG, IMP, IgA, IgD and IgE. In case of IgG, it has two light chains (L chains) of polypeptide having a molecular weight of about 25,000 and two heavy chains (H chains) of polypeptide having a molecular weight of about 51,000. Between H-L chains and between H-H chains, there is usually present a disulfide bond connecting two chains. An amino acid sequence consisting of about 100 amino acids at N terminal of each of the H and L chains is antigen-specific and represents an antigen-binding site. This part is called a variable (V) region. Subsequent amino acid sequence consisting of 400 amino acids in H chain or 150 amino acids in L chain is called a constant (C) region which is identical among all immunoglobulins belonging to a Ig Class such as IgG or IgM Class, or those belonging to a subclass such as $igG_1$ or $IgG_2$. It is known that human IgG may have $C\kappa$ or $C\lambda$ in L chain and $C\gamma1$, $C\gamma2$, $C\gamma3$ or $C\gamma4$ in H chain. L and H chains having one of these identified partial structures are called $\kappa$, $\lambda$, $\gamma1$, $\gamma2$, $\gamma3$ and $\gamma4$ chain, respectively.

H and L chain contain "domain structures". For instance, H chain is composed of VH, CH1, CH2, CH3 domains and hinge regions connecting CH1 and CH2 domains.

The variable region comprises four framework regions in which relatively conservative amino acid sequences are retained among various antibodies and three CDRs which are relatively variable in the amino acid sequence among different antibodies. In one molecule of an antibody which comprises two H chains and two L chains, there ar present six CDRs originated from VH and VL regions, which take steric configurations closely approached one another to form an antigen binding site.

The summary of the structure and function of the antibody is as above.

The monoclonal antibody (hereinafter, referred to as "MAb") is widely used for diagnosis and therapy in the medical field and as reagents, affinity column materials, etc. in the industrial field. The mouse MAb is readily obtained by the mouse/mouse hybridoma method.

For preparation of a human MAb which is more valuable for human therapy that a mouse MAb, various improvements have been proposed but any reliable method for establishing a producible cell line with good reproducibility and high efficiency has not been established. Because of this reason, human MAb as clinically usable is quite restricted. Also, the production of a human antibody to an antigen originated from a human being is generally impossible except any special case.

In case of a mouse, MAb specific to various antigens including antigens of human origin can be easily obtained but on administration to a human being, a problem of antigenicity occurs. Some attempts have been made to produce an antibody lowered in antigenicity to a human body from mouse MAb. Specifically, attempts are directed to the production of a humanized antibody wherein only a CDR, which is said to form an antigen-binding site, in the variable region of mouse MAb, is left and all the other regions are replaced by the human ones.

For instance, in the method as disclosed in EP-A-87302620, the CDR of mouse MAb is transplanted into the human MAb V region by the use of site specific mutation with a long oligonucleotide. As an example of obtaining a humanized antibody as explained above, there is known an attempt for humanization of rat MAb Campath-1 recognizing CDw52 antigen on human T calls (EP-A-89301291).

As one of mouse MAbs for which humanization would be effective, there is known anti-human IL-2 receptor antibody B-B10 (Japanese Patent Publication (Unexamined) No. 2-13371). This antibody is antagonistic to the binding of IL-2 to the IL-2 receptor on human T-cells and inhibits the IL-2 dependent growth of activated T-cells. It also inhibits the human mixed lymphocyte reaction. Accordingly, said MAb is useful for treatment and prevention of the diseases caused by graft-versus-host reaction or host-versus-graft reaction, prevention of rejection on the transplantation of bone marrow, kidney, heart, lung, pancreas, skin, liver, etc., therapy of T-cell dependent allergy or autoimmune diseases (E.g., myocarditis, diabetes mellitus, myasthenia gravis, lupus erythematosus, Crohn disease, multiple sclerosis, AIDS, Meningitis, Arthritis) and therapy of tumors expressing IL-2 receptor such as T-cell leukemia.

In fact, the administration of B-B10 on the graft-versus-host reaction as produced after the bone marrow transplantation or the preventive administration of B-B10 on the rejection of the liver transplantation produces a certain effect (Blood, Vol. 75, 1017 (1990); Lancet, Vol. 335, 1596 (1990)).

On the practical therapy, however, the administration of B-B10 is carried out only for a short period of time, because of a concern to the antigenicity of mouse MAb. Also, there is a clinical example where an antibody to mouse MAb was found from a patient to whom mouse MAb was administered. The administration over a long period of time is thus quite difficult from the practical viewpoint. As understood from this, the administration of B-B10 is limited due to the fact that it is a kind of mouse MAb and the therapeutic effect is also restricted.

In order to solve the above problem, it is necessary to decrease the antigenicity originated from the mouse antibody by humanization. As to humanized antibodies, there are present some other examples in addition to those as hereinabove mentioned. For instance, an anti-Tac antibody is humanized by transplantation of nine amino acid residues on the framework in addition to CDR, and as the result of the humanization, the activity is lowered to ⅓ (Proc. Natl. Acad. Sci. USA Vol. 86, 10029 (1989)). Also, the humanized antibodies to the gB glycoprotein and gD glycoprotein of herpes simplex virus are transplanted respectively with two amino acids residues and eight amino acid residues on the framework in addition to CDR, and their activities are respectively ½ and 1 in comparison with mouse MAb (Proc. Natl. Acad. Sci. USA, Vol. 88, 2869 (1991)). Further, the humanized antibody to the human CD4 is transplanted with one amino acid residue in addition to CDR, and its activity is ⅓ in comparison with mouse MAb (Proc. Natl. Acad. Sci. USA, Vol. 88, 4181 (1991)).

As understood from the above, it is necessary for obtaining a humanized antibody having an activity similar to mouse MAb to transplant not only CDR but also an amino acid residue(s) which would afford an important influence on the antigen-antibody binding in the framework of mouse MAb. However, such amino acid residue(s) are different depending upon the kind of the antibody; in fact, the examples as above recited shown that some amino acid residues are common to them and some others are not. It is thus required to determine the necessary amino acid residue (s) on each antibody. Like the case of the humanized antibody to the gD glycoprotein of herpes simplex virus, such an approach as leaving the amino acid sequence on the framework expected to participate in the antigen-antibody binding as in mouse MAb. In this case, however, the same amino acid residue as in mouse MAb increase so that the antigenicity of mouse MAb is increased.

When the framework of mouse MAb contains one or more amino acid residues which rarely exist in human antibodies, they are, in principle, concerted to other amino acid residues highly common to human antibodies. Thus, sixteen amino acid residues on the framework have been substituted in this case. As understood from the above, it is necessary for obtaining a humanized antibody to identify amino acid residue(s) on the framework which appear essential for retaining the activity and to transplant them to the human antibody together with CDR. However, it is very difficult to pre-determine such essential amino acid residue (s). Accordingly, transplantation of all of the amino acid residues on the framework, which appear possibly involved in antigen-binding activity, is desirable in preparing humanized antibody. However, the humanized antibody thus prepared is destined to include many amino acid residues derived from mouse antibody, and therefore, antigenicity of the humanized antibody may inevitably be high.

DISCLOSURE OF THE INVENTION

Under the circumstances as noted above, the present inventors attempted the humanization of mouse B-B10. As the result, it has been succeeded to produce humanized B-B10 having an activity similar to mouse B-B10 with transplantation of a minimum amino acid sequence in the framework. Namely, the cDNA of the V region of the antibody was successfully cloned from the hybridoma cell line producing mouse B-B10 by a per se conventional procedure such as the polymerase chain reaction (PCR) method, and the amino acid sequence was determined. Then, the V region of human antibody having a high homology to such amino acid sequence was selected, and the framework of this human antibody was bound with the B-B10 V region CDR and a part of the framework to design several kinds of the humanized B-B10 V region. Such humanized B-B10 is different from mouse B-B10 in the amino acid residue of the framework of which a part was transplanted. The DNA sequence encoding said amino acid residues was synthesized, and a plasmid expressing humanized B-B10 was constructed. The plasmid was introduced into a mouse myeloma cell line to obtain a humanized B-B10 producing cell.

Productivity of the antibody was increased by amplification of the antibody-encoding gene, and the resultant several humanized B-B10 antibodies were purified and evaluated on their activities. As a result, the amino acid residues on the framework, which have strong influence on the B-B10 activity and which are called "M5", were clarified. The most active humanized B-B10 was expected to be the one in which as much amino acid residues as possible on the framework of mouse B-B10, including M5, were transplanted. However, contrary to expectation, the evaluation of the activities revealed that humanized B-B10 obtained by minimum level of transplantation was most active as far as it includes M5. This humanized antibody (M5) is expected to be advantageous with respect to antigenicity, and yet it showed almost the same level of activity as that of mouse B-B10. The present invention is based on this finding.

Since the gene encoding humanized B-B10 has been determined, the preparation of various humanized B-B10 derivatives has become possible by means of recombinant DNA technology. Such B-B10 derivatives include Fv, Fab, and a fuzed protein consisting of the humanized B-B10 and a proteinaceous toxin or an enzyme.

The present invention is explained in more detail below.

The present invention provides humanized antibodies derived from mouse anti-human IL-2 receptor antibody, B-B10 MAb. One embodiment of the antibodies of the invention is defined by the following CDR in V region and partial amino acid sequences in the framework.

H chain V region

CDR1: SEQ ID No. 1

CDR2: SEQ ID No. 2

CDR3: SEQ ID No. 3

L chain V region

CDR1: SEQ ID No. 4

CDR2: SEQ ID No. 5

CDR3: SEQ ID No. 6

H chain V region

27th–30th amino acids: SEQ ID No. 7

94th amino acid: Arg

L chain V region

49th amino acid: Lys

The present invention further provides humanized antibodies defined by the V region sequences as indicated below.

H chain V region: SEQ ID No. 8

L chain V region: SEQ ID No. 9.

The present invention includes a matured (perfect) hunanized B-B10 antibody and its fragments such as Fv, Fab, (Fab)'$_2$.

The hunanized antibody and its fragment of the invention may contain an additional functional molecule. For instance, they may be bound to a functional molecule such as a toxin (e.g. lysin), an enzyme, or a certain kind of cytokine.

BRIEF DESCRIPTIONS OF DRAWINGS

FIG. 1 (SEQ ID NOS: 37 and 38) shows DNA sequence encoding mouse B-B10 V region (H chain), and amino acid sequence encoded thereby.

FIG. 2 (SEQ ID NOS: 39 and 40) shows DNA sequence encoding mouse B-B10 V region (L chain), and amino acid sequence encoded thereby.

FIG. 3 shows comparison of the amino acid sequence of humanized B-B10M0 with the amino acid sequences of mouse B-B10, and human antibodies KAS (SEQ ID NO:41) and PAY (SEQ ID NO:42) which were used as templates. Position of mutation of M1-5 is also indicated. In M1-5, all of the amino acid residues shown in the figure are replaced by the amino acid residues of mouse B-B10. FR means framework.

FIG. 4 (SEQ ID NO:34) shows synthesized DNA sequence of humanized B-B10M0 V region (H chain). The framed sequence codes for V region. Other sequence comes from FK-001 antibody gene. The underline indicates the position of a primer used in the gene synthesis.

FIG. 5 (SEQ ID NO:36) shows synthesized DNA sequence of humanized B-B10M0 V region (L chain). The framed sequence codes for V region. Other sequence comes from FK-001 antibody gene. The underline indicates the position of a primer used in the gene synthesis.

Figure 6A:
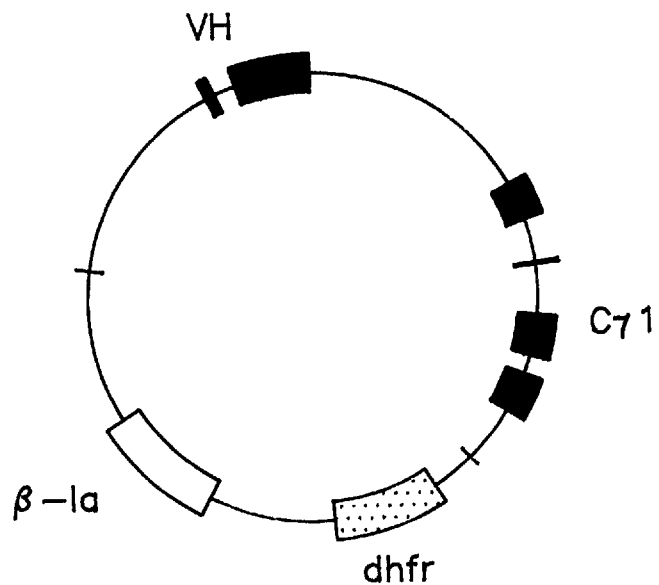
Figure 6B:
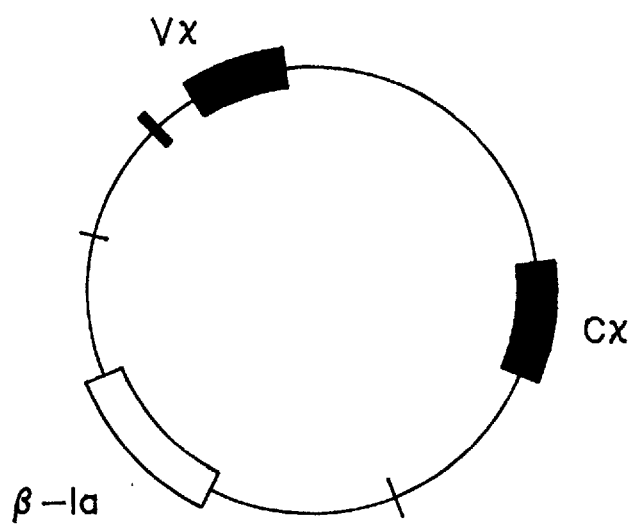

FIG. 6 (a) shows humanized B-B10 H chain expression plasmid, and (b) shows humanized B-B10 L chain expression plasmid. The symbols, B-1a and dhfr respectively mean lactamase gene and dihydro folate reductase gene. VH, VK, Cγ1, and Ck respectively mean H chain V region gene, k chain V region gene, γ1 chain constant region gene, and k chain constant region gene.

Figure 7:
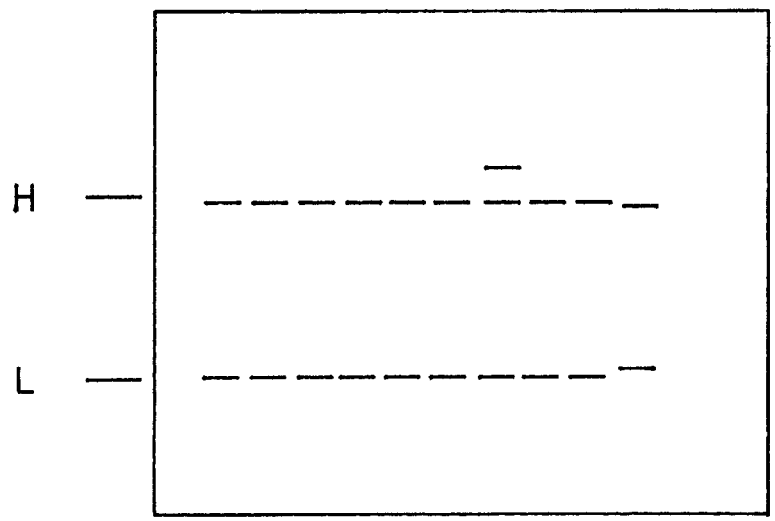

FIG. 7 shows SDS polyacrylamide gel electrophoresis of purified humanized B-B10. Lanes from left to right correspond to M0, M1, M2, M3, M4, M5, M123, M45, M12345, and mouse B-B10. H and L show the position of H chain and L chain respectively.

FIG. 8 shows inhibition of IL-2 dependent T-cell proliferation due to humanized B-B10. OD value on the ordinate is an index for the number of alive cells.

FIG. 9 shows inhibition of IL-2 dependent T-cell proliferation due to humanized B-B10. OD value on the ordinate is an index for the number of alive cells.

According to the present invention, humanized B-B10 antibody may be prepared by:

1) constructing a gene encoding a humanized antibody in which at least CDR in V region is derived from mouse B-B10 MAb and other part is derived from human antibody;
2) inserting the gene encoding the humanized antibody into a vector capable of existing in a host cell to obtain an expression plasmid;
3) transfecting the host cell with the plasmid to establish a humanized B-B10 MAb producing cell; and
4) cultivating the cell to produce humanized B-B10 MAb.

The production of humanized antibody of the invention with the aid of recombinant DNA technology is explained below.

(i) Isolation of RNA from the hybridoma producing mouse B-B10 antibody

Several conventional methods are available for isolation of RNA from the hybridoma producing mouse B-B10 antibody. However, the principal procedures common to them are cell lysis in the presence of a protein denaturing agent (e.g. guanidine thiocyanate), and isolation of RNA by phenol extraction or cesium chloride density-gradient centrifugation. Oligo-dT cellulose column chromatography is useful for further purification, if desired. Standard protocol for the procedures is found in a text book, for example, J. Sambrook; Molecular Cloning, A Laboratory Manual, 2nd Ed., 1989, Cold Spring Harbor Laboratory Press, USA. Example 1 hereinafter described gives one example for the isolation.

(ii) Isolation and Identification of V region cDNA

V region cDNA may be prepared from the RNA isolated in (i) using a primer specific to mouse V region and a reverse transcriptase. The V region cDNA thus obtained may be amplified by means of Polymerase Chain Reaction (PCR) using a specific primer. The primer specific to mouse v region may be prepared according to the teaching of M. J. Coloma, Biotechniques, Vol.11, 1991, p.152; R. Orlandi et al, Proc. Natl. Aca. Sci. USA, Vol.86, 1989, p.3833; or L. Sastry, Pro. Natl. Aca. Sci. USA, Vol.86, 1989, p.5728. Detailed explanation for PCR is given in the aforementioned J. Sambrook's text, particularly in Chapter 14. The V region cDNA thus obtained may be cloned using a plasmid or a phage vector. The amino acid sequence of the cloned cDNA may be determined by dideoxy sequencing (J. Messing, Method in Enzymology, Vol.101, 1983, p.20) or Maxam-Gilbert method (A. M. Maxam & W. Gilbert, Proc. Natl. Aca. Sci. USA, Vol.74, 1977, p.560). Based on the DNA sequence determined, corresponding amino acid sequence can be deduced. Part of the deduced amino acid sequence can be confirmed to be correct by comparison with corresponding partial amino acid sequence of the antibody peptide, which has been determined by a protein sequencer. The amino acid sequence of mouse B-B10 V region thus identified is shown in FIGS. 1 and 2.

(iii) Design of amino acid sequence of humanized B-B10 V region

A human antibody, into which the mouse B-B10 CDR is to be transplanted, may be selected using a database such as Genbank or EMBL. A human antibody V region having a high homology to the amino acid sequence of mouse B-B10 V region is selected. Specifically, KAS antibody for VH and PAY antibody for Vk are recommended. As for the amino acid residues on the framework, which are to be transplanted like CDR, one can take it into consideration that the amino acid residues which is suspected to influence on the formation of CDR's three-dimensional structure have been determined with some accuracy on the basis of the analysis of a three-dimensional structure of a known antibody (canonical structure model; Nature, Vol.342, 1989, p.877). Additional useful information is that the amino acid residues in the framework, which exist close to CDR, may have influence on the CDR's three-dimensional structure. Three-dimensional structure of a designed humanized B-B10 V region can be predicted using an appropriate computer program, preferably BIOCES available from Sumitomo Chemical Company, Limited and Sumitomo Pharmaceuticals Company, Limited. Exemplary design for humanized antibodies of the invention is shown in FIG. 3 of the accompanying drawings and Example 5.

(iv) Construction of DNA encoding V region of humanized B-B10

A DNA encoding V region of humanized B-B10 may be constructed by a total synthesis or repeated PCR using a mouse B-B10 or human V region DNA as a template. Additional DNA sequences necessary for expression, such as signal sequence and intron, may be linked to the DNA encoding V region of humanized B-B10 at the 5' or 3' terminal. Example 6 hereinafter described illustrates the synthesis of DNA for humanized B-B10 V region by means of PCR using a mouse B-B10 V region DNA as a template and linkage of the resultant DNA to the DNA encoding the V region of human antibody FK-001 (Japanese Patent Publication (Unexamined) No. 267295/1988) at the 5' or 3' terminal.

An arbitrary amino acid sequence in V region can be changed to a desired sequence using site-directed mutagenesis in vitro.

Various humanized B-B10 V region DNAs obtained in the manner as described above are illustrated in Example 7.

(v) Construction of expression plasmid for humanized B-B10

If necessary, a translation-initiating signal, a transcription-initiating signal (promoter), an enhancer, etc. may be added to the humanized B-B10 V region DNA. Specific examples of promoters and enhancers are, for example, SV40 (J. Mol. Appl. Genet., Vol.1, 1983, p.327), the promoter/enhancer derived from cytomegalovirus (Cell, Vol.41, 1985, p.521), LTR from Rous sarcoma virus (Proc. Natl. Aca. Sci. USA, Vol.76, 1982, p.6777). Example 6 demonstrates the use of the promoter/enhancer of the gene for human FK-001 antibody. Linkage of human B-B10 V region DNA at the downstream with a gene for a constant (c) region provides a humanized antibody gene.

Constant region genes are available from JCRB. The humanized B-B10 H chain and L chain may be introduced into separate or same vector(s) to construct an expression plasmid. Examples of the expression vectors are SV40-derived vector (J. Mol. Appl. Genet., Vol.1, 1982, p.327), and bovine papilloma virus vector (Proc. Natl. Aca. Sci. USA, Vol.79, 1982, p.7147). Examples 8 and 9 demonstrate the use of pSV2dhfr (Mol. Cell. Biol., Vol.1, 1981, p.854) and pUC118 (Methods Enzymol., Vol.153, 1987, p.3) respectively.

(vi) Transfection of humanized B-B10 expression plasmid

Humanized B-B10 antibody-producing cells capable of expressing humanized B-B10 antibody gene may be obtained by means of a conventional DNA introduction using an animal cell not producing antibodies, preferably mouse myeloma cell. The expression plasmid for the humanized B-B10 antibody gene may be introduced, together with a marker plasmid if desired, into a host cell through conventional procedures such as red cell ghost method (Proc. Natl. Acad. Sci. USA., Vol.77, 1980, p.2163), DEAE-dextran method (Nature, Vol.293, 1981, p.79), calcium phosphate method (Virology, Vol.52, 1973, p.456), protoplast fusion method (Cell, Vol.33, 1981, p.717), electroporation method (Proc. Natl. Aca. Sci. USA, Vol.81, 1984, p.7161), and lipofection method (Proc. Natl. Acad. Sci. USA, Vol.84, 1987, p.7413).

DNA-introduced cells may be selected by cultivating the transfected cells in a selective medium containing G-418 or mycophenolic acid. Humanized B-B10 antibody in a culture supernatant may be detected by enzyme immunoassay (e.g. ELISA), and a humanized B-B10 producing cell can be selected from drug-resistant cells. By cultivating the humanized B-B10-producing cell, humanized B-B10 can be obtained from the supernatant and purified using conventional chromatography. Productivity of the antibody may be enhanced by using a marker capable of gene-amplification and adding a selective drug to the culture medium, whereby amplification of the antibody gene is induced. Examples 10, 12 and 13 demonstrate the construction of humanized B-B10 expression plasmid using an expression unit of FK-001 antibody gene, the establishment of humanized B-B10 producing cell by transfection of mouse myeloma cell, Sp2/0-Ag14 (available from ATCC) as a host cell, and recovery of humanized B-B10.

Purified humanized B-B10 may be formulated by conventional methods usually employed in the production of a biological preparation. In essence, the purified antibody is sterile-filtered, for instance, with a membrane filter, followed by addition of a stabilizer.

(vii) Evaluation of humanized B-B10

Enzyme immunoassay, particularly ELISA, may be used for evaluation of humanized B-B10 (E. Harlow and D. Lane; Antibodies: A Laboratory Manual, 1988, Cold spring Harbor Laboratory, USA; especially Paragraph 14). The amount of the antibody present in a culture medium may be determined by ELISA which uses a plate on which an antibody against H chain C region has been adsorbed.

Biological activity of humanized B-B10 may be measured by determining the inhibition of IL-2 dependent proliferation of activated human T cell as illustrated in Examples 11 and 14.

The humanized B-B10 antibody of the invention is parenterally administered with a dosage of about 0.05–500 mg for treatment and prevention of diseases caused by graft-versus-host reaction or host-versus-graft reaction, prevention of rejection on the transplantation of bone marrow, kidney, heart, lung, pancreas, skin, liver, etc., therapy of T-cell dependent allergy or autoimmune diseases (e.g. myocarditis, diabetes mellitus, myasthenia gravis, lupus erythematosus, Crohn disease, multiple sclerosis, AIDS, meningitis, arthritis), and therapy of tumors expressing IL-2 receptor such as T-cell leukemia.

ADVANTAGEOUS EFFECT OF THE INVENTION

1) Half-life of mouse Mab in blood is about 15 hours, when administered to human (J. Natl. Cancer Inst., Vol.80, 937, 1988), whereas half-life of human IgG1 is about 2 weeks. The humanized antibody of the invention is very close to human antibody, and therefore, may possibly have similar half-life to human antibody. It is expected that the humanized B-B10 has much longer half-life in blood and remains effective for a prolonged period of time when compared with mouse B-B10.

2) The effect described in the above item 1) enables to decrease frequency of administration and dosage of the antibody.

3) Antigenicity of humanized B-B10 is much less than mouse B-B10. As a matter of fact, administration of humanized antibody, Campath-1H, did not induce anti-Campath-1H antibody in two instances (Lancet, Vol.2, 1394, 1988).

Accordingly, it is expected that humanized B-B10, when administered to human, is not likely to induce undesirable neutralization antibody, contrary to mouse B-B10. This permits frequent administration of humanized B-B10 for a long time, which increases therapeutical effects and enlarges the scope of applications.

The present invention will be hereinafter explained in detail by way of examples, but is not limited to those examples.

EXAMPLE 1

Extraction and Purification of RNA from a B-B10-Producing Hybridoma

Hybridomas which produce B-B10 was suspended in 4M guanidine thiocyanate (60° C.) and treated with a syringe attached with a 18 G needle to lower the viscosity. To the suspension was added one equivalent of phenol (60° C.) and the mixture shaked vigorously. After the addition of ¼ volume of 0.1M sodium acetate (pH 5.2)/10 mM Tris-HCl (pH 7.4)/1 mM EDTA and ½ volume of a mixture of chloroform/isoamyl alcohol (24:1), the suspension was shaked vigorously, ice-cooled and centrifuged. The aqueous phase was taken and RNA was recovered by ethanol precipitation.

EXAMPLE 2

Cloning of cDNA Encoding V Region of B-B10

Two cDNAs each encoding VH and Vk region of mouse B-B10 were synthesized using specific primer, amplified by PCR, cloned, and sequenced as follows. Primers "VHback" and "VHfor" which anneal to the N- and C-termini of VH respectively, and primers "Vkfor" and "Vkback" which anneal to N- and C- termini of Vk respectively, were synthesized using an Applied Biosystems Model 380A DNA synthesizer. Sequences of these primers are shown below.

VHback: SEQ ID No.10
   SEQ ID No.11
VHfor: SEQ ID No.12
   SEQ ID No.13
Vkback: SEQ ID No.14
   SEQ ID No.15
VKfor: SEQ ID No.16

B-B10 RNA was primed with VHfor primer to yield B-B10 VH cDNA, which was followed by PCR using VHfor and VHback primers. B-B10RNA was primed with Vkfor primer to yield B-B10 Vk cDNA, which was followed by PCR using Vkfor and Vkback primers. The cDNA was synthesized in a 20 μl reaction mixture containing 50 mM KCl, 10 mM Tris HCl (pH8.3), 1.5 mM MgCl$_2$, 0.001% gelatin, each 0.8 mM of dATP, dGTP, dCTP and dTTP, 2 μl RNA, and 1 μM primer in the presence of 20 units reverse transcriptase (RAV-2, Takara Shuzo) for 30 min at 42° C. After heating the mixture at 95° C. for 5 min, PCR was carried out in a 100 μl reaction mixture containing 50 mM KCl, 10 mM Tris HCl (pH8.3), 1.5 mM MgCl$_2$, 0.001% gelatin, each 0.4 mM of dATP, dGTP, dCTP and dTTP using 1 μM primer by repeating 40 times of a reaction cycle consisting of heating at 95° C. for 30 sec, 55° C. for 30 sec and 72° C. for 1 min. The products of PCR were then 5'-end phosphorylated using T4 polynucleotide kinase (Takara Shuzo) and cloned into the Hinc II site of plasmid vector pUC19. The DNA sequence was determined by dideoxy method using a commercially available primer for the vicinity of the multi-cloning sites and a Sequenase Version 2.0 DNA Sequencing Kit (United States Biochemical Corporation, USA) according to the manufacturer's recommended protocols. The identified sequences of DNA and deduced amino acid might be incorrect at the N and C terminal regions. However, a correct sequence of the N-terminal region of Vk was obtained without the aid of primer because the Vkback primer annealed to the upper site from 5' terminal of Vk. The correct sequences were thereafter obtained as described in Examples 3 and 4 and provided in the accompanying drawings, FIGS. 1 and 2.

EXAMPLE 3

Confirmation of the Amino Acid Sequence of the N-terminal Regions of Mouse B-B10 VH by Means of Gas-Phase Protein Sequencer Purified mouse B-B10 antibody was mixed with an equivalent amount of a loading buffer (125 mM Tris-HCl, pH 6.8, 4% sodium dodecyl sulfate(SDS), 10% mercaptoethanol, 0.01% bromophenolblue(BPB)). After heating at 100° C. for 5 min, the mixture was electrophoresed on 12.5% polyacrylamide gel (SDS-PAGE), electroblotted onto PVDF membrane (Millipore, USA) in a 10 mM CAPS (3-cyclohexylaminopropane sulfate, Dojin Chemicals, Inc.) and visualized by staining with Coomassie Brilliant Blue R 250 Wako Junyaku, Japan). The band containing H chain was excised and the N-terminal amino acid sequences of collected peptide fragments were determined by means of an Applied Biosystems model 470A/120A gas-phase protein sequencer (J.Biol.Chem., 262:10035 (1987)). The results are shown below. VH N-terminal amino acid sequence: SEQ ID No.17

EXAMPLE 4

Confirmation of the Amino Acid Sequence of the C-terminal Regions of Mouse B-B10 VH and Vk The DNA sequences each encoding the C-terminal region of mouse B-B10 VH and Vk were amplified by PCR, cloned and sequenced. Primers VH2, MIG-1, Vk2 and MIK-1 which anneal to VHCDR1, N-terminal region of CH1, VkCDR1 and N-terminal region of Ck, respectively, were synthesized. Sequences of these primers are shown below.

VH2: SEQ ID No.18
Vk2: SEQ ID No.19
MIG-1: SEQ ID No.20
MIK-1: SEQ ID No.21

B-B10 RNA was primed with MIG-1 primer to yield B-B10 VH cDNA, which was followed by PCR using VH2 and MIG-1 primers. B-B10 RNA was primed with MIK-1 primer to yield B-B10 Vk cDNA, which was followed by PCR using Vk2 and MIK-1 primers. The cDNA was synthesized in a 50 μl of a reaction mixture containing 50 mM KCl, 10 mM Tris-HCl (pH8.3), 1.5 mM MgCl$_2$, 0.001% gelatin, each 0.2 mM of dATP, dGTP, dCTP and dTTP, 21 μl RNA, and 1 μM primer in the presence of 20 units reverse transcriptase (RAV-2, Takara Shuzo) for 1 hr at 42° C. After heating the mixture at 95° C. for 10 min, 10 μl of the reaction mixture was subject to PCR, which was conducted in a 100 μl reaction mixture containing 50 mM KCl, 10 mM Tris-HCl (pH8.3), 1.5 mM MgCl$_2$, 0.001% gelatin, each 0.4 mM of dATP, dGTP, dCTP and dTTP, and 1 μM primer by repeating 30 times of a reaction cycle consisting of heating at 95° C. for 1 min, 50° C. for 1 min and 72° C. for 2 min. The products of PCR were separated by a gel-electrophoresis and the desired product was extracted from the gel and purified. The resultant product of PCR was 5'-end phosphorylated using T4 polynucleotide kinase (Takara Shuzo) and cloned into Hinc II site of plasmid vector pUC19. The cloned DNA was sequenced by dideoxy method using a commercially available primer for the vicinity of the multi-cloning sites and a Sequenase Version 2.0 DNA Sequencing Kit (Unite States Biochemical Corporation, USA) according to the manufacturer's recommended protocols. The identified DNA sequence and deduced amino acid sequence are contained in the sequences shown in FIGS. 1 and 2.

EXAMPLE 5

Design for the Amino Acid Sequence of Humanized B-B10 VH and VK Regions

Prinas Data Base was searched for the VH region of human antibody having an amino acid sequence which has the highest homology with the amino acid sequence of mouse B-B10 VH region to select the VH region of human antibody KAS (63% homology). VK region of a human antibody PAY which has the highest homology with Vk region of mouse B-B10 Vk region (57.0% homology) was also selected and obtained in the same manner. Humanized B-B10 V region was designed by combining the frameworks of these human antibodies to mouse B-B10 CDR except that the amino acids located at Nos. 27 to 30 and 94 which are positioned within frameworks were remained to be those of mouse B-B10. This is because the amino acids were selected from frameworks which affect on the structure of CDR according to the canonical structure model. The resultant humanized B-B10 was designated as M0. Variants were also obtained by changing amino acid(s) of humanized B-B10 to that of mouse. Thus, by replacing the amino acid(s) of VH region of humanized B-B10 with mouse amino acid(s), following variants were prepared. M1: at No.48; M2 at Nos. 66 and 67; and M3 at No.105. By replacing the amino acids of Vk region of humanized B-B10 with mouse amino acid(s), following variants were prepared. M4 at Nos. 1 and 3; and M5 at No. 49. In the variants in M1, 2, 3 and 5, amino acids to be changed were selected because they are close to the CDR and therefore may affect on the structure of CDR. Amino acid(s) which gives a significant difference between mouse B-B10 and M0 in the comparison of the predicted steric structures obtained by BIOCES was considered to have a reverse effect on the activity and therefore it was changed to that of mouse. As a result, M4 and M5 were selected. The variants having the above M1, M2 and M3 was designated as M123, that having the M4 and M5 designated as M45, and that having the M1, M2, M3, M4 and M5 designated as M12345. The above-mentioned names were used for expressing amino acid variants themselves, antibodies containing the same, and strains producing the antibodies in common. The relationships between these amino acid sequences are provided in FIG. 3. Amino acids were numbered according to the teaching of Kabat et al (Sequences of Proteins of Immunological Interest, 4th edition, 1987, NIH, USA).

EXAMPLE 6

Synthesis of Humanized B-B10 M0 by PCR

Humanized B-B10 VH and Vk genes were synthesized by PCR using cDNA encoding mouse B-B10 VH and Vk regions and a gene encoding FK-001 human antibody (Biotechnology, volume 7, pp. 805–810 (1989)). The DNA sequence of humanized B-B10 V region was designed as shown in FIG. 4 and 5 so that a signal peptide and/or intron originated from a gene encoding FK-001 antibody might ligate to the 5' and 3' of the region encoding humanized B-B10 V region. The resultant gene contained DNA encoding VH and the DNA encoding Vk, each of which can be isolated as a SacI-BalI fragment and Bam HI-HindIII fragment, respectively for the cloning. The primers shown in the FIGS. 4 and 5 were used to obtain mouse VH and Vk DNAs, and PCR was conducted using as the template a gene encoding FK-001 antibody, successively. Primers within the V region can anneal to mouse V region gene within the CDR region. The conditions used for the PCR is the same as that described in Example 3. Short PCR products were synthesized and the neighboring two products were combined to obtain a template for the next PCR, and so on. Finally, PCR products containing the desired gene encoding the V region of humanized B-B10 were obtained and cloned into phage vector M13mp19 or plasmid vector pUC18. The DNA sequence of cloned PCR product was determined by dideoxy method using a commercially available primer (Takara Shuzo) for the vicinity of the multi-cloning sites and a Sequenase Version 2.0 DNA Sequencing Kit (United States Biochemical Corporation, USA) according to the manufacturer's recommended protocols.

The synthesized gene encoding humanized B-B10 VH region was excised as a SacI-BalI fragment and inserted into the SacI-BalI site of a VH gene fragment of FK-001 antibody, and finally, was cloned into pUC18 as a 5.2 kb BamHI-HindIII fragment containing FK001 VH promoter, VH region-encoding gene of humanized B-B10, and IgH enhancer. The resultant plasmid was designated as plasmid phB-B10VHEM0.

Plasmid phB-B10VkM0 was constructed by inserting a 1.5 kb BamHI-BamHI fragment containing FK-001 Vk gene promoter to a BamHI site of plasmid pUC18 which comprises humanized B-B10 Vk region-encoding gene cloned into the BamHI-HindIII site.

EXAMPLE 7

Introduction of Mutations M1, M2, M3, M4 and M5 into VH and VK Regions of Humanized B-B10 by In Vitro Site-specific Mutagenesis A 5.2 kb BamHI-HindIII fragment containing VH gene of B-B10, H-chain promoter, and H-chain enhancer was obtained by digesting plasmid phB-B10VHEM0 with restriction enzymes BamHI and HindIII, subjecting to the electrophoresis on agarose gel, and extracting the DNA fragment by Geneclean II.

The DNA fragment was then inserted into BamHI-HindIII site of charomid pUC118 (Takara Shuzo) to obtain plasmid phB-B10VHE (118). In the same manner as above, plasmid phB-B10Vk (118) was obtained by transferring 2.1 kb SacI-HindIII fragment containing Vk gene of plasmid phB-B10VkM0 to pUC118. These plasmids were transformed into E. coli MV1184 (Nihon Gene). The resultant transformants were transfected with helper phage M13KO7 (Takara Shuzo) and cultured to give phage-like particles containing circular single-stranded DNA. After the purification of phage-like particles, the circular single-stranded DNAs contained therein were extracted and purified to use as a template for the in vitro site-specific mutagenesis. The preparation of the circular single-stranded DNA was conducted according to the protocol attached to the pUC118 products from the supplier. DNA primers used for the in vitro site-specific mutagenesis were synthesized and purified. Nucleotide sequences of these DNAs are shown below.

Primer for mutation M1: SEQ ID No.22
Primer for mutation M2: SEQ ID No.23
Primer for mutation M3: SEQ ID No.24
Primer for mutation M4: SEQ ID No.25
Primer for mutation M5: SEQ ID No.26

In vitro site-specific mutagenesis was carried out using primer M1, M2 or M3 when the template was phB-B10VHE (118), and primer M4 or M5 when the template was phB-B10Vk(118). The primer and the template was mixed and incubated at 70° C. for 3 min, and then at 37° C. for 30 min for the annealing. The annealed product was then reacted in the presence of dCTPαS, 6 units of Klenow fragment and 6 units of T4 DNA ligase at 16° C. for 15 hr for the elongation and ligation and the unreacted template DNAs were removed. The template DNA was nicked by treating with restriction enzyme NciI (5 units) at 37° C. for 90 min. Most of the template DNAs were removed by treating with 50 units of ExoIII nuclease at 37° C. for 30 min. At the end of the process, the resultant product was reacted in the presence of 3 units E. coli DNA polymerase I and 2 units of T4 DNA ligase at 16° C. for 3 hr to obtain a mutation-introduced circular double-stranded DNA. In the above procedures, reagents, buffers, and column for purification were obtained from Oligonucleotide-directed in vitro mutagenesis system version 2 (Amersham, Inc.) and used according to the protocol provided by the supplier. The reaction mixture containing the mutation-introduced DNA was used to transform into E. coli JM109 to prepare plasmid DNA. The DNA was used to confirm the DNA sequence at the site of mutation by means of dideoxy sequencing method. For the sequencing, the above-mentioned M1, M2, M3, M4 or M5 primer, or commercially available primer (Takara Shuzo) in the vicinity of the multi-cloning site of pUC 19 was used as a primer and Sequenase Version 2.0 DNA Sequencing Kit (United states Biochemical Corporation, USA) was used for the reaction. These are used according to the protocol provided by the supplier. Multiple mutagenesis for M123 and M45 were conducted by repeating the above-mentioned procedures. The sites of mutations are given in FIG. 3.

EXAMPLE 8

Construction of H Chain Expression Plasmid

Plasmids phB-B10VHEM0, M1, M2, M3, and M123 each containing 5.2 kb BamHI-Hind III fragment which encodes VH gene of various B-B10, H chain promoter, and H chain enhancer were digested with Bam HI and Hind III, and the resultant fragments were subjected to agarose gel electrophoresis to separate the above-noted desired fragment, which was then extracted and purified by means of Geneclean II. Another plasmid containing a separately cloned gene encoding the constant region of human γ1 chain (Cγ1) was digested with Hind III and EcoRI and subjected to agarose gel electrophoresis to separate 16.9 kb Hind III-EcoRI fragment containing Cγ1 gene, which was then extracted and purified by means of Geneclean II. In the same manner as above, 4.2 kb Bam HI-EcoRI fragment was separated from plasmid pSV2dhfr and purified.

The above-noted three DNA fragments were combined and linked together using T4 DNA ligase to obtain plasmids phB-B10dhfr HG1M0, M1, M2, M3, and M123 which express various B-B10 H chains.

EXAMPLE 9

Construction of k Chain Expression Plasmid

Plasmid containing the cloned FK-001 k chain gene (Biotechnology, Vol.7, 1989, pp.805–810) was digested with restriction enzyme Hind III, and the digest products were electrophoresed on agarose gel to separate 5.6 kb Hind III-Hind III fragment containing k chain constant region (Ck) gene, which was then extracted and purified using Geneclean II. Plasmids phB-B10VkM0, M4, M5 and M45 each containing a Vk gene of various B-B10 were digested with restriction enzyme Hind III followed by BAP treatment. The plasmids and the 5.6 kb Hind III-Hind III fragment were treated with T4 DNA ligase, resulting in insertion of the 5.6 kb Hind III-Hind III fragments into the Hind III site of each of the plasmids to obtain expression plasmids of various B-B10K chains, phB-B10HKM0, M4, M5 and M45.

EXAMPLE 10

Establishment of Various B-B10 Antibodies Producing Cell Lines by Lipofectin Method Mouse myeloma cell line Sp2/0-Ag14 (Sp2/0, ATCC CRL-1581) was cultured in Dulbecco's modified Eagle's medium (DMEM, Nissui, Japan) supplemented with 10% fetal calf serum (FCS, Hyclone, USA) until it reached to logarithmic growth phase. From the culture, $5 \times 10^6$ cells were harvested by centrifugation, suspended in 0.5 ml of serum-free medium (Celgrosser H, Sumitomo Pharmaceuticals) and placed into a well on a 6-well plate. Ten μg of each of H Chain Expression Plasmids, 10 μg of L chain expression plasmid, and 5 μg of pSV2neo were digested with restriction enzyme PvuI (Takara Shuzo) to generate lenear DNAs, and then ethanol precipitated to recover the DNAs. The DNAs were suspended in 250 μl of Celgrosser H.

Fifty μl of lipofectin was diluted with 200 μl of Celgrosser H, and mixed with the DNA solution above to prepare the DNA/lipofectine complex. The DNA/lipofectin complex was dropwise added to the cell on 6-well plate, and the resulting mixture was incubated at 37° C. under 5% $CO_2$ atmosphere for 7 hours. The cell was harvested, suspended in DMEM containing 10% FCS at a cell density of 5–10× $10^4$/ml, and the suspension was dispensed in an amount of 100 μl per well on a 96-well plate. After 1–2 days, 100 μl of DMEM containing 800 μg/ml G-418 (Gibco, USA) and 10% FCS was added to each well. Thereafter, half of the medium was replaced with DMEM containing 400 μg/ml G-418 and 10% FCS every 2–3 days. Eight G-418 resistant colonies were found after about 2 weeks cultivation. Amount of the antibody in culture supernatant from each well was determined by Enzyme-linked immunosorbent assay (ELISA) as described in the following Example, and the wells which contained relatively high concentration of antibody were selected, and the cells from such wells were pooled for use as the antibody-producing cell.

EXAMPLE 11

Determination of the Amount of Humanized B-B10 (Human IgG (γ, k)) by ELISA

Determination of the amount of humanized B-B10 (human IgG (γ, k)) was accomplished as follow.

Anti-human IgG (γ chain) antibody (Cappel, USA) was dissolved in phosphate buffer (pH7.2, NaCl (8g/1), KCl (0.2 g/l), $NaHPO_4 \cdot 12H_2O$ (0.2 g/l) and $KH_2PO_4$ (0.2 g/l)) (PBS) at a concentration of 10 μg/ml, and placed on 96-well microplate (Falcon, USA) ("microplate") in an amount of 100 μl per well and then incubated at 37° C. for 2 hours.

One hundred-twenty μl of PBS solution containing 1% bovine serum albumin (BSA) was added to each well and incubated at 37° C. for 2 hours to block the protein-unbound area on the microplate.

Samples to be assayed for the amount of the antibody were suitably diluted with PBS containing 0.05% Tween 20 (hereinafter referred to as PBST), and added to each well at a ratio of 100 μl per well and incubated at 37° C. for 2 hours. After the incubation, samples were removed and wells were washed 3 times with PBST followed by the addition of 100 μl per well of the second antibody solution and subsequent incubation at 37° C. for 2 hours. As the second antibody, phosphatase-labeled affinity-purified anti-human immunoglobulin k chain antibody (Tago, USA) was utilized. After removing the second antibody and washing 3 times with PBST, 100 μl of color-developing substrate (1 mg/ml disodium P-nitrophenylphosphate in 10% diethanolamine buffer (pH 9.1) containing $NaN_3$ (0.2 mg/ml) and $MgCl_2 \cdot 6H_2O$ (0.1 mg/ml)) was added to each well and reacted at 37° C. After the reaction, optical density of each well was measured at 405 nm using Multiscan (Titertek).

This assay only allows the measurement of the normal human Ig in which γ chain and k chain associate each other.

EXAMPLE 12

Amplification of the Antibody Gene by the Use of MTX and the Increased Production of the Antibody The antibody-producing cell described in the preceding Example was suspended in DMEM/10% FCS containing 50 nM MTX (methotrexate, Gibco, USA) at $1-5 \times 10^5$ cells/ml, and the 100–200 μl aliquot was dispensed in each well on 96-well multiplate and then cultured at 37° C. under 5% CO atmosphere. After about 2 weeks cultivation, the amount of the antibody in culture supernatant from each well was determined by ELISA in accordance with Example 11.

Cells were collected only from the wells which displayed a high OD value, i.e., a high production level of the antibody, and cultured in larger scale to establish a 50 nM MTX-resistant cell line. Similarly, a 100 nM, 200 nM, or 400 nM MTX-resistant cell line was established in the same manner as in the 50 nM-resistant cell line.

Antibody concentration of the culture supernatant from each of the cell lines was determined by ELISA using as a standard purified M0 antibody which had been affinity-purified through Protein A-column as described in the subsequent Example.

The results are shown in the following Table 1.

TABLE 1

| Antibody produced | Concentration of antibody (μg/ml) | | | | |
|---|---|---|---|---|---|
| | 0 | 50 | 100 | 200 | 400 (nMMTX) |
| M0 | 0.8 | 7.4 | 8.7 | 14.7 | — |
| M1 | not determined | 2.6 | — | — | 3.6 |
| M2 | 0.1 | 2.7 | — | 9.0 | — |
| M3 | 0.1 | 0.3 | — | 1.0 | — |
| M4 | 0.3 | 3.5 | — | — | 9.5 |
| M5 | 0.2 | 3.4 | — | — | 5.3 |
| M123 | 1.1 | 4.0 | — | 8.0 | — |
| M45 | 0.2 | 1.8 | — | 1.7 | — |
| M12345 | 0.7 | 1.8 | — | — | 4.5 |

In these cell lines, an increased amount of the antibody was produced with a cell line of increased MTX-resistance. These,MTX-resistant cell lines were cultured in larger scale and finally subcultivated once in serum-free medium (Cellgrowther-H, Sumitomo Pharmaceuticals) to obtain serum-free culture supernatant.

EXAMPLE 13

Purification of Antibodies

Serum-free culture supernatant containing various B-B10 antibodies was filtered through filter unit (Nalge, USA) having a pore size of 0.22 μm and applied to Protein A-cellophaine column (0.5 ml) (Seikagaku Kogyo, Japan) at a flow rate of 1–2ml/min. After washing the column with 10 ml of Immuno Pure™ Binding Buffer (Pierce, USA), the antibodies bond to the column were eluted with 2 ml of Immuno Pure™ Elution Buffer (Pierce, USA). The eluent was neutralized with 0.2 ml of 1M Tris-HCl (pH8.0), dialized against PBS, and sterilized by filtration using a filter having a pore size of 0.22 μm to obtain purified B-B10. Colorimetric analysis using BCA™ Protein Assay Reagent (Pierce, USA) and purified bovine IgG (BioRad, USA) as a standard determined a protein content of the purified B-B10. The results are shown in Table 2.

TABLE 2

| Antibody | Volume of Culture Supernatant (ml) | Final Volume (ml) | Protein Concentration (μg/ml) | Protein Content (μg) |
|---|---|---|---|---|
| M0 | 70 | 2.8 | 105 | 294 |
| M1 | 130 | 2.8 | 76 | 193 |
| M2 | 130 | 1.0 | 370 | 370 |
| M3 | 270 | 2.8 | 99 | 277 |
| M4 | 130 | 2.8 | 470 | 1316 |
| M5 | 130 | 2.8 | 129 | 361 |
| M123 | 150 | 2.8 | 92 | 258 |
| M45 | 310 | 2.8 | 183 | 512 |
| M12345 | 140 | 2.8 | 119 | 333 |

The above samples were subjected to SDS polyacrylamide gel electrophoresis according to the method described in Example 3. All of the samples except M123 showed no band other than H and L chain bands, which revealed that the samples had been sufficiently purified. The amount of the contaminant which caused the extra band observed in M123 was very small, and therefore, it is thought harmless in evaluating the activity of the sample.

EXAMPLE 14

Evaluation of Biological Activities of Various Variant B-B10 Antibodies

Biological activities of various purified B-B10 obtained in the preceding Examples were studied. Evaluation of biological activities of various B-B10 was carried out by comparing their activities in inhibiting proliferation of IL-2 dependent human activated T cells. Thus, human T cells activated by phytohemagglutinin (PHA) and recombinant human IL-2 (Colaborative Research, USA) were plated onto 96-well multiplate (Falcon, USA) for cell culture at final concentrations of $4-10 \times 10^4$ cells/100 μl/well and 0.25 ng/100 1l/well, respectively. After addition of B-B10 samples of various concentrations, the plate was incubated at 37° C. for three days under 5% $CO_2$. To each of the wells was added 20 μl of 2.5 mg/ml MTT (3-(4,5-dimethylthiazol-2-yl)-2,5-diphenyl tetrazolium bromide, suspended in PBS), and four-hour cultivation was conducted at 37° C. under 5% $CO_2$. Formazan generated in living cells was dissolved in 40 mM HCl/isopropanol which had been added to the wells at 100 μl/well. $OD_{570}$ for each well was determined using $OD_{630}$ as a reference and used as an indication of the number of living cells. The results are shown in FIG. 8, which shows that Proliferation of T cells is inhibited depending on the concentration of B-B10. Among humanized B-B10 antibodies, M5 showed the highest inhibitory activity, which was estimated as nearly equal to that of mouse B-B10 after comparison of their working concentrations. M5 activity was higher than those of multiple variants M45 and M12345 containing M5.

We claim:

1. A humanized antibody having a specific binding activity to human IL-2 receptor, wherein the variable region has the following amino acid sequence:
H chain V region: SEQ ID No.8
L chain V region: SEQ ID No.9.

2. A humanized antibody of claim 1 further comprising a human γ1 constant region (Cγ1) and a human κ constant region (Cκ).

3. A fragment of the humanized antibody according to claim 1 or 2, wherein said fragment is selected from the group consisting of an (Fab')$_2$, an Fab and an Fv.

4. A humanized antibody according to claim 1, which is bound with a functional molecule.

5. A process for producing a humanized antibody, which comprises preparing a plasmid expressing a humanized antibody according to claim 1 or 2, introducing the plasmid into a host cell, obtaining a stable transformant cell and cultivating the resulting cell producing the humanized antibody.

6. A process according to claim 5, wherein the host cell is an animal or human call.

7. A cDNA encoding a humanized antibody having a specific binding activity to human IL-2 receptor, which comprises the following DNA sequences coding variable regions:

H chain V region: SEQ ID No.34

L chain V region: SEQ ID No.35.

8. A process for producing a humanized antibody, which comprises preparing a plasmid having a cDNA according to claim 7, introducing the plasmid into a host cell, obtaining a stable transformant cell and cultivating the resulting cell producing the humanized antibody.

9. A therapeutic composition, to be administered parentally to a patient in need thereof, comprising an effective amount of a humanized antibody of claim 1 or 2 and a pharmaceutically acceptable carrier thereof.

10. A therapeutic composition to be administered parenterally to a patient in need thereof, comprising an effective amount of a fragment of a humanized antibody of claim 3 and a pharmaceutically acceptable carrier thereof.

11. A humanized antibody fragment according to claim 3 which is bound with a functional molecule.

12. A humanized antibody according to claim 2, which is bound with a functional molecule.

* * * * *

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:1:

Asp Thr Tyr Met His
   1               5

( 2 ) INFORMATION FOR SEQ ID NO:2:

( i ) SEQUENCE CHARACTERISTICS:
      ( A ) LENGTH: 17 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:2:

Arg Ile Asn Pro Thr Asn Gly Asn Thr Lys Tyr Asp Pro Lys Phe Gln
   1               5                   10                  15

Gly ( 2 ) INFORMATION FOR SEQ ID NO:3:

( i ) SEQUENCE CHARACTERISTICS:
      ( A ) LENGTH: 9 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:3:

Arg Gly Asp Ala Met Tyr Phe Asp Val
   1               5

( 2 ) INFORMATION FOR SEQ ID NO:4:

( i ) SEQUENCE CHARACTERISTICS:
      ( A ) LENGTH: 11 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:4:

Arg Ala Ser Gln Thr Ile Gly Thr Ser Ile His
   1               5                   10

( 2 ) INFORMATION FOR SEQ ID NO:5:

( i ) SEQUENCE CHARACTERISTICS:
      ( A ) LENGTH: 7 amino acids
      ( B ) TYPE: amino acid
      ( C ) STRANDEDNESS: Not Relevant -continued (D) TOPOLOGY: linear (ii) MOLECULE TYPE: peptide (xi) SEQUENCE DESCRIPTION: SEQ ID NO:5:

```
Tyr Ala Ser Glu Ser Ile Ser
1               5
```

(2) INFORMATION FOR SEQ ID NO:6:

(i) SEQUENCE CHARACTERISTICS:
    (A) LENGTH: 9 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:6:

```
Gln Gln Ser Ser Ser Trp Pro Leu Thr
1               5
```

(2) INFORMATION FOR SEQ ID NO:7:

(i) SEQUENCE CHARACTERISTICS:
    (A) LENGTH: 4 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:7:

```
Phe Asn Ile Lys
1
```

(2) INFORMATION FOR SEQ ID NO:8:

(i) SEQUENCE CHARACTERISTICS:
    (A) LENGTH: 118 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:8:

```
Glu Val His Leu Val Gln Ser Gly Ala Glu Val Lys Lys Pro Gly Ser
1               5                   10                  15
Ser Val Lys Val Ser Cys Lys Ala Ser Gly Phe Asn Ile Lys Asp Thr
                20                  25                  30
Tyr Met His Trp Val Arg Gln Ala Pro Gly Gln Gly Leu Glu Trp Met
            35                  40                  45
Gly Arg Ile Asn Pro Thr Asn Gly Asn Thr Lys Tyr Asp Pro Lys Phe
        50                  55                  60
Gln Gly Arg Val Thr Ile Thr Ala Asp Glu Ser Thr Asn Thr Ala Tyr
65                  70                  75                  80
Met Glu Leu Arg Ser Leu Arg Ser Asp Asp Thr Ala Met Tyr Tyr Cys
                85                  90                  95
Ala Arg Arg Gly Asp Ala Met Tyr Phe Asp Val Thr Gly Gln Gly Thr
                100                 105                 110
Leu Val Thr Val Ser Ser
            115
```

(2) INFORMATION FOR SEQ ID NO:9:

( i ) SEQUENCE CHARACTERISTICS:
  ( A ) LENGTH: 107 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:9:

| Glu | Ile | Val | Leu | Thr | Gln | Ser | Pro | Gly | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Gln | Thr | Ile | Gly | Thr | Ser |
|---|---|---|---|---|---|---|---|---|---|---|---|---|---|---|---|
| | | | 20 | | | | | 25 | | | | | 30 | | |

| Ile | His | Trp | Tyr | Gln | Gln | Arg | Pro | Gly | Gln | Ala | Pro | Arg | Leu | Leu | Ile |
|---|---|---|---|---|---|---|---|---|---|---|---|---|---|---|---|
| | | 35 | | | | | 40 | | | | | 45 | | | |

| Lys | Tyr | Ala | Ser | Glu | Ser | Ile | Ser | Gly | Ile | Pro | Asp | Arg | Phe | Ser | Gly |
|---|---|---|---|---|---|---|---|---|---|---|---|---|---|---|---|
| | | 50 | | | | 55 | | | | | 60 | | | | |

| Ser | Gly | Ser | Gly | Thr | Asp | Phe | Thr | Leu | Thr | Ile | Ser | Arg | Leu | Glu | Pro |
|---|---|---|---|---|---|---|---|---|---|---|---|---|---|---|---|
| 65 | | | | | 70 | | | | | 75 | | | | | 80 |

| Glu | Asp | Phe | Ala | Val | Tyr | Tyr | Cys | Gln | Gln | Ser | Ser | Ser | Trp | Pro | Leu |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Val | Glu | Ile | Leu |
|---|---|---|---|---|---|---|---|---|---|---|
| | | | 100 | | | | | 105 | | |

( 2 ) INFORMATION FOR SEQ ID NO:10:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

AGGTCAAACT GCAGCAGTCA GG 22

( 2 ) INFORMATION FOR SEQ ID NO:11:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

AGGTGCAGCT TCTCGAGTCT GG 22

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

ACGGTGACCG TGGCGCCTTG 20

( 2 ) INFORMATION FOR SEQ ID NO:13:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:13:

ACGGTGACCG AGGAGCCTTG                    20

( 2 ) INFORMATION FOR SEQ ID NO:14:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:14:

GCTGACACAG TCTCCA                         16

( 2 ) INFORMATION FOR SEQ ID NO:15:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:15:

GATCACCCAG ACTCCA                         16

( 2 ) INFORMATION FOR SEQ ID NO:16:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:16:

CTCCAGCTTG GTCCC                          15

( 2 ) INFORMATION FOR SEQ ID NO:17:

( i ) SEQUENCE CHARACTERISTICS:
      ( A ) LENGTH: 20 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:17:

Glu Val Gln Leu Gln Gln Ser Gly Ala Glu Leu Val Lys Ser Gly Ala
1               5                   10                  15

Ser Val Lys Leu
            20

( 2 ) INFORMATION FOR SEQ ID NO:18:

( i ) SEQUENCE CHARACTERISTICS:

(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

AACATTAAAG ACACCTATAT GCAC 24

(2) INFORMATION FOR SEQ ID NO:19:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

CAGTCAGACC ATTGGCACAA GCATACAC 28

(2) INFORMATION FOR SEQ ID NO:20:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

AGGGAAATAG CCCTTGACCA GGCA 24

(2) INFORMATION FOR SEQ ID NO:21:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

GACATTGATG TCTTTGGGGT AGAA 24

(2) INFORMATION FOR SEQ ID NO:22:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

GATTAATTCT TCCTATCCAC TCCAGGCC 28

(2) INFORMATION FOR SEQ ID NO:23:

(i) SEQUENCE CHARACTERISTICS:
(A) LENGTH: 28 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:23:

GCTGTAATAG TGGCCTTGCC CTGGAACT 28

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:24:

GACCAGGGTG CCTGCGCCCC AGACATCG 28

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:25:

ACTGAGTCAG GAGGATGTCC CCGTAGGC 28

(2) INFORMATION FOR SEQ ID NO:26:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:26:

CTCAGAAGCA TATTTTATGA GAAGCCTT 28

(2) INFORMATION FOR SEQ ID NO:27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:27:

GACACCTATA TGCAC 15

(2) INFORMATION FOR SEQ ID NO:28:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:28:

AGAATTAATC CTACGAATGG TAATACTAAA TATGACCCGA AGTTC 45

( 2 ) INFORMATION FOR SEQ ID NO:29:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

AGGGGGGATG CCATGTACTT CGATGTC        27

( 2 ) INFORMATION FOR SEQ ID NO:30:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

AGGGCCAGTC AGACCATTGG CACAAGCATA CAC        33

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TATGCTTCTG AGTCTATCTC T        21

( 2 ) INFORMATION FOR SEQ ID NO:32:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CAACAAAGTA GTAGCTGGCC GCTCACG        27

( 2 ) INFORMATION FOR SEQ ID NO:33:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

TTCAACATTA AA        12

( 2 ) INFORMATION FOR SEQ ID NO:34:

( i ) SEQUENCE CHARACTERISTICS:

( A ) LENGTH: 354 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:34:

| | | | | | | |
|---|---|---|---|---|---|---|
| GAGGTGCACC | TGGTCCAGTC | AGGGGCAGAG | GTCAAGAAGC | CAGGGTCCTC | AGTCAAGGTC | 60 |
| TCCTGTAAGG | CTTCTGGCTT | CAACATTAAA | GACACCTATA | TGCACTGGGT | GAGGCAGGCC | 120 |
| CCTGGGCAGG | GCCTGGAGTG | GATGGGAAGA | ATTAATCCTA | CGAATGGTAA | TACTAAATAT | 180 |
| GACCCGAAGT | TCCAGGGCAG | GGTCACTATT | ACAGCAGACG | AGTCCACAAA | CACAGCCTAC | 240 |
| ATGGAGCTGA | GGAGCCTGAG | GTCTGATGAC | ACTGCCATGT | ATTACTGTGC | TAGGAGGGGG | 300 |
| GATGCCATGT | ACTTCGATGT | CTGGGGCCAA | GGCACCCTGG | TCACCGTCTC | CTCA | 354 |

( 2 ) INFORMATION FOR SEQ ID NO:35:

( i ) SEQUENCE CHARACTERISTICS:
( A ) LENGTH: 321 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:35:

| | | | | | | |
|---|---|---|---|---|---|---|
| GAGATCGTCC | TGACTCAGTC | TCCAGGCACA | CTGTCTCTGA | GTCCAGGAGA | AAGAGCCACA | 60 |
| CTGTCCTGCA | GGGCCAGTCA | GACCATTGGC | ACAAGCATAC | ACTGGTATCA | GCAGAGACCA | 120 |
| GGCCAGGCCC | CAAGGCTTCT | CATAAAGTAT | GCTTCTGAGT | CTATCTCTGG | CATCCCTGAT | 180 |
| AGGTTTAGTG | GCAGTGGATC | AGGGACAGAT | TTTACTCTTA | CAATCTCCAG | GCTGGAGCCA | 240 |
| GAAGATTTCG | CAGTCTATTA | CTGTCAACAA | AGTAGTAGCT | GGCCGCTCAC | GTTCGGTCAG | 300 |
| GGGACCAAGG | TCGAGATAAA | A | | | | 321 |

( 2 ) INFORMATION FOR SEQ ID NO:36:

( i ) SEQUENCE CHARACTERISTICS:
( A ) LENGTH: 321 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:36:

| | | | | | | |
|---|---|---|---|---|---|---|
| GAGATCGTCC | TGACTCAGTC | TCCAGGCACA | CTGTCTCTGA | GTCCAGGAGA | AAGAGCCACA | 60 |
| CTGTCCTGCA | GGGCCAGTCA | GACCATTGGC | ACAAGCATAC | ACTGGTATCA | GCAGAGACCA | 120 |
| GGCCAGGCCC | CAAGGCTTCT | CATATATTAT | GCTTCTGAGT | CTATCTCTGG | CATCCCTGAT | 180 |
| AGGTTTAGTG | GCAGTGGATC | AGGGACAGAT | TTTACTCTTA | CAATCTCCAG | GCTGGAGCCA | 240 |
| GAAGATTTCG | CAGTCTATTA | CTGTCAACAA | AGTAGTAGCT | GGCCGCTCAC | GTTCGGTCAG | 300 |
| GGGACCAAGG | TCGAGATAAA | A | | | | 321 |

( 2 ) INFORMATION FOR SEQ ID NO:37:

( i ) SEQUENCE CHARACTERISTICS:
( A ) LENGTH: 354 base pairs
( B ) TYPE: nucleic acid
( C ) STRANDEDNESS: single
( D ) TOPOLOGY: linear (i i) MOLECULE TYPE: DNA (genomic)

(i x) FEATURE:
    (A) NAME/KEY: CDS
    (B) LOCATION: 1..354

(x i) SEQUENCE DESCRIPTION: SEQ ID NO:37:

```
GAG GTG CAG CTG CAG CAG TCA GGG GCA GAG CTT GTG AAG TCA GGG GCC      48
Glu Val Gln Leu Gln Gln Ser Gly Ala Glu Leu Val Lys Ser Gly Ala
 1               5                  10                  15

TCA GTC AAG TTG TCC TGT ACA GCT TCT GGC TTC AAC ATT AAA GAC ACC      96
Ser Val Lys Leu Ser Cys Thr Ala Ser Gly Phe Asn Ile Lys Asp Thr
             20                  25                  30

TAT ATG CAC TGG GTG AAG CAG AGG CCT GAA CAG GGC CTG GAG TGG ATT     144
Tyr Met His Trp Val Lys Gln Arg Pro Glu Gln Gly Leu Glu Trp Ile
         35                  40                  45

GGA AGA ATT AAT CCT ACG AAT GGT AAT ACT AAA TAT GAC CCG AAG TTC     192
Gly Arg Ile Asn Pro Thr Asn Gly Asn Thr Lys Tyr Asp Pro Lys Phe
     50                  55                  60

CAG GGC AAG GCC ACT GTG ACA GCA GAC ACA TCC TCC AAC ACA GCC TAC     240
Gln Gly Lys Ala Thr Val Thr Ala Asp Thr Ser Ser Asn Thr Ala Tyr
 65                  70                  75                  80

CTG CAG CTC GGC AGC CTG ACA TCT GAG GAC ACT GCC GTC TAT TAC TGT     288
Leu Gln Leu Gly Ser Leu Thr Ser Glu Asp Thr Ala Val Tyr Tyr Cys
                 85                  90                  95

GCT AGG AGG GGG GAT GCC ATG TAC TTC GAT GTC TGG GGC GCA GGG ACC     336
Ala Arg Arg Gly Asp Ala Met Tyr Phe Asp Val Trp Gly Ala Gly Thr
             100                 105                 110

ACG GTC ACC GTC TCC TCA                                             354
Thr Val Thr Val Ser Ser
             115
```

(2) INFORMATION FOR SEQ ID NO:38:

(i) SEQUENCE CHARACTERISTICS:
        (A) LENGTH: 118 amino acids
        (B) TYPE: amino acid
        (D) TOPOLOGY: linear (i i) MOLECULE TYPE: protein (x i) SEQUENCE DESCRIPTION: SEQ ID NO:38:

```
Glu Val Gln Leu Gln Gln Ser Gly Ala Glu Leu Val Lys Ser Gly Ala
 1               5                  10                  15

Ser Val Lys Leu Ser Cys Thr Ala Ser Gly Phe Asn Ile Lys Asp Thr
             20                  25                  30

Tyr Met His Trp Val Lys Gln Arg Pro Glu Gln Gly Leu Glu Trp Ile
         35                  40                  45

Gly Arg Ile Asn Pro Thr Asn Gly Asn Thr Lys Tyr Asp Pro Lys Phe
     50                  55                  60

Gln Gly Lys Ala Thr Val Thr Ala Asp Thr Ser Ser Asn Thr Ala Tyr
 65                  70                  75                  80

Leu Gln Leu Gly Ser Leu Thr Ser Glu Asp Thr Ala Val Tyr Tyr Cys
                 85                  90                  95

Ala Arg Arg Gly Asp Ala Met Tyr Phe Asp Val Trp Gly Ala Gly Thr
             100                 105                 110

Thr Val Thr Val Ser Ser
             115
```

(2) INFORMATION FOR SEQ ID NO:39:

(i) SEQUENCE CHARACTERISTICS:

(A) LENGTH: 321 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..321

(xi) SEQUENCE DESCRIPTION: SEQ ID NO:39:

```
GAC ATC TTG CTG ACT CAG TCT CCA GCC ATC CTG TCT GTG AGT CCA GGA    48
Asp Ile Leu Leu Thr Gln Ser Pro Ala Ile Leu Ser Val Ser Pro Gly
120             125             130

GAA AGA GTC AGT TTC TCC TGC AGG GCC AGT CAG ACC ATT GGC ACA AGC    96
Glu Arg Val Ser Phe Ser Cys Arg Ala Ser Gln Thr Ile Gly Thr Ser
135             140             145             150

ATA CAC TGG TAT CAG CGA AGA ACA AAT GGT TCT CCA AGG CTT CTC ATA   144
Ile His Trp Tyr Gln Arg Arg Thr Asn Gly Ser Pro Arg Leu Leu Ile
                155             160             165

AAG TAT GCT TCT GAG TCT ATC TCT GGG ATC CCT TCC AGG TTT AGT GGC   192
Lys Tyr Ala Ser Glu Ser Ile Ser Gly Ile Pro Ser Arg Phe Ser Gly
170             175             180

AGT GGA TCA GGG ACA GAT TTT ACT CTT AGC ATC AAC AGT GTG GAG TCT   240
Ser Gly Ser Gly Thr Asp Phe Thr Leu Ser Ile Asn Ser Val Glu Ser
185             190             195

GAA GAT ATT GCA GAT TAT TAC TGT CAA CAA AGT AGT AGC TGG CCG CTC   288
Glu Asp Ile Ala Asp Tyr Tyr Cys Gln Gln Ser Ser Ser Trp Pro Leu
200             205             210

ACG TTC GGT GCT GGG ACC AAG CTG GAG CTG AAA                       321
Thr Phe Gly Ala Gly Thr Lys Leu Glu Leu Lys
215             220             225
```

(2) INFORMATION FOR SEQ ID NO:40:

(i) SEQUENCE CHARACTERISTICS:
(A) LENGTH: 107 amino acids
(B) TYPE: amino acid
(D) TOPOLOGY: linear (ii) MOLECULE TYPE: protein (xi) SEQUENCE DESCRIPTION: SEQ ID NO:40:

```
Asp Ile Leu Leu Thr Gln Ser Pro Ala Ile Leu Ser Val Ser Pro Gly
1               5               10              15

Glu Arg Val Ser Phe Ser Cys Arg Ala Ser Gln Thr Ile Gly Thr Ser
                20              25              30

Ile His Trp Tyr Gln Arg Arg Thr Asn Gly Ser Pro Arg Leu Leu Ile
                35              40              45

Lys Tyr Ala Ser Glu Ser Ile Ser Gly Ile Pro Ser Arg Phe Ser Gly
            50              55              60

Ser Gly Ser Gly Thr Asp Phe Thr Leu Ser Ile Asn Ser Val Glu Ser
65              70              75              80

Glu Asp Ile Ala Asp Tyr Tyr Cys Gln Gln Ser Ser Ser Trp Pro Leu
                85              90              95

Thr Phe Gly Ala Gly Thr Lys Leu Glu Leu Lys
                100             105
```

(2) INFORMATION FOR SEQ ID NO:41:

(i) SEQUENCE CHARACTERISTICS:
(A) LENGTH: 121 amino acids
(B) TYPE: amino acid (C) STRANDEDNESS: Not Relevant
(D) TOPOLOGY: linear (i i) MOLECULE TYPE: peptide (x i) SEQUENCE DESCRIPTION: SEQ ID NO:41:

```
Glu Val His Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Gln Ala Asn Tyr Ala Gln Lys Phe
    50              55                  60
Gln Gly Arg Val Thr Ile Thr Ala Asp Glu Ser Thr Asn Thr Ala Tyr
65              70                  75                  80
Met Glu Leu Arg Ser Leu Arg Ser Asp Asp Thr Ala Met Tyr Tyr Cys
                85                  90                  95
Ala Lys Glu Gly Tyr Gly Asp Tyr Gly Arg Pro Phe Asp Phe Trp Gly
            100                 105                 110
Gln Gly Thr Leu Val Thr Val Ser Ser
            115                 120
```

(2) INFORMATION FOR SEQ ID NO:42:

(i) SEQUENCE CHARACTERISTICS:
(A) LENGTH: 108 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:42:

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Arg Pro Gly Gln Ala Pro Arg Leu Leu
        35                  40                  45
Ile Tyr Gly Ala Ser Ser Arg Ala Thr Gly Ile Pro Asp Arg Phe Ser
    50              55                  60
Gly Ser Gly Ser Gly Thr Asp Phe Thr Leu Thr Ile Ser Arg Leu Glu
65              70                  75                  80
Pro Glu Asp Phe Ala Val Tyr Tyr Cys Gln Gln Tyr Gly Ser Ser Pro
                85                  90                  95
Leu Thr Phe Gly Gln Gly Thr Lys Val Glu Ile Lys
            100                 105
```